US00PP25329P2

(12) United States Plant Patent
van den Top

(10) Patent No.: US PP25,329 P2
(45) Date of Patent: Mar. 3, 2015

(54) *HEUCHERA* PLANT NAMED 'SILVER BLUSH'

(50) Latin Name: *Heuchera×hybrida*
Varietal Denomination: Silver Blush

(71) Applicant: Hendrik Jan van den Top, Barneveld (NL)

(72) Inventor: Hendrik Jan van den Top, Barneveld (NL)

( * ) Notice: Subject to any disclaimer, the term of this patent is extended or adjusted under 35 U.S.C. 154(b) by 141 days.

(21) Appl. No.: 13/986,662

(22) Filed: May 22, 2013

(51) Int. Cl.
*A01H 5/00* (2006.01)

(52) U.S. Cl.
USPC ..... Plt./440

(58) Field of Classification Search
CPC ..... A01H 5/02; A01H 5/12; A01H 5/00; A01H 5/025
USPC ..... Plt./440
See application file for complete search history.

*Primary Examiner* — June Hwu
(74) *Attorney, Agent, or Firm* — Audrey Charles

(57) ABSTRACT

A new and distinct cultivar of *Heuchera* plant named 'Silver Blush', characterized by its silver-colored foliage with contrasting dark venation, pink-colored flowers, and moderately vigorous, compact-mounded growth habit, is disclosed.

1 Drawing Sheet

Latin name of genus and species of plant claimed: *Heuchera×hybrida.*

Variety denomination: 'Silver Blush'.

BACKGROUND OF THE INVENTION

The present invention relates to a new and distinct cultivar of *Heuchera* plant botanically known as *Heuchera×hybrida* and hereinafter referred to by the cultivar name 'Silver Blush'.

The new *Heuchera* plant was discovered and selected in June 2009 as an individual seedling from a population of seedlings by the Inventor in a controlled nursery environment in Barneveld, The Netherlands. The parentage is unknown.

Asexual reproduction of the new *Heuchera* by divisions in a controlled environment in Barneveld, The Netherlands and by in vitro propagation since April 2011, has shown that the unique features of the *Heuchera* are stable and reproduced true to type in successive generations.

SUMMARY OF THE INVENTION

The following characteristics of the new cultivar have been repeatedly observed and can be used to distinguish 'Silver Blush' as a new and distinct cultivar of *Heuchera* plant:

1. Silver-colored foliage with contrasting dark venation;
2. Pink-colored flowers: and
3. Moderately vigorous, compact-mounded growth habit.

Of the many commercially available *Heuchera* cultivars, the most similar in comparison to the new cultivar is 'Silver Scrolls', U.S. Plant Pat. No. 12,066. However, in comparison, plants of the new cultivar differ from plants of 'Silver Scrolls' in at least the following characteristics:

1. Plants of the new cultivar have less dark-colored venation giving a more silver appearance than plants of 'Silver Scrolls'; and
2. Plants of the new cultivar have a flower color that is different from plants of 'Silver Scrolls'.

In addition, plants of the new cultivar are similar to 'Silver Indiana', not patented. However, in comparison, plants of the new cultivar differ from plants of 'Silver Indiana' in at least the following characteristics:

1. Plants of the new cultivar have less dark-colored venation giving a more silver appearance than plants of 'Silver Indiana'; and
2. Plants of the new cultivar have a flower color that is different from plants of 'Silver Indiana'.

BRIEF DESCRIPTION OF THE PHOTOGRAPHS

The accompanying photographs show, as nearly true as it is reasonably possible to make the same in color illustrations of this type and typical foliage characteristics of the new cultivar. Colors in the photographs differ slightly from the color values cited in the detailed description, which accurately describes the colors of 'Silver Blush'. The plants were grown in one-gallon containers for approximately 2 years in a greenhouse in Barneveld, The Netherlands.

DETAILED BOTANICAL DESCRIPTION

Figure 1:
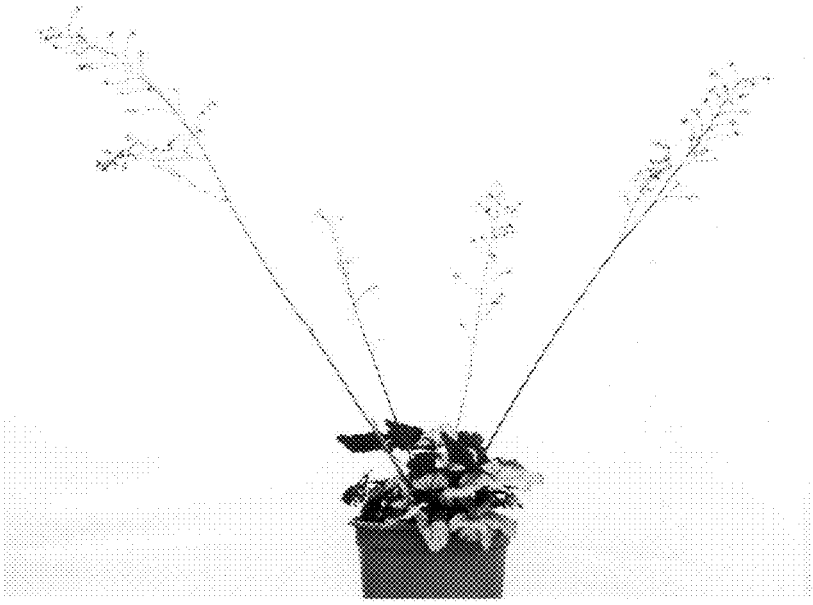
FIG. 1 illustrates a side view of the overall growth habit of 'Silver Blush'.
Figure 2:
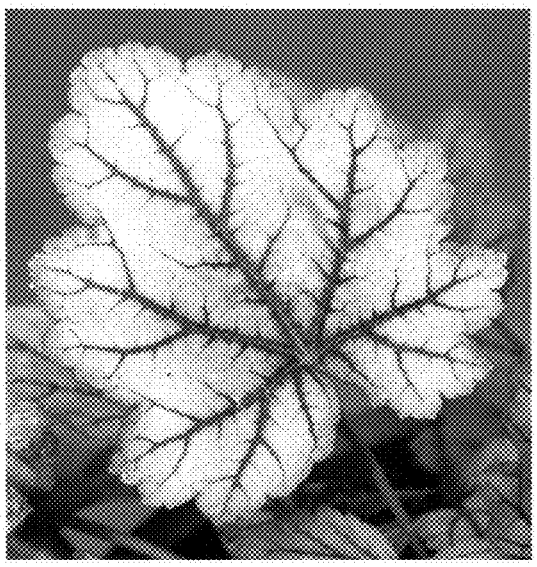
FIG. 2 illustrates a close-up view of an individual leaf of 'Silver Blush'.
Figure 3:
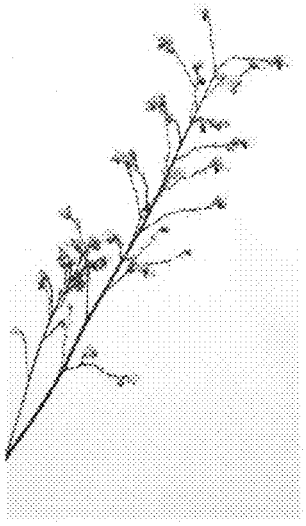
FIG. 3 illustrates a close-up view of an individual inflorescence of 'Silver Blush'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in April 2012 under natural light conditions.

The data which define these characteristics were collected from asexual reproductions carried out in Barneveld, The Netherlands and grown under conditions comparable to those used in commercial practice. The plants were grown in one-gallon containers for approximately 2 years utilizing a soilless growth medium under average day temperatures of 14° C. to 28° C. and average night temperatures of 5° C. to 18° C. No pinching, growth retardants or photoperiodic treatments were used. Observations were made when the plants were in natural daylight conditions.

Botanical classification: *Heuchera×hybrida* cultivar Silver Blush.

Parentage:

*Female parent*.—Unknown *Heuchera*×hybrid.

*Male parent*.—Unknown *Heuchera*×hybrid.

Propagation:

*Type*.—In vitro propagation is preferred, divisions are possible.

*Time to initiate roots in vitro*.—Approximately 10 days at 20° C.

*Time to initiate roots in greenhouse*.—Approximately 30 days at 21° C.

*Time to produce a rooted plantlet in summer*.—Approximately 42 days.

*Root description*.—Medium thickness, fibrous; grey in color.

*Rooting habit*.—Freely branching, sparse density.

Plant description:

*Commercial crop time*.—Approximately 20 weeks from a rooted tissue culture plantlet to finish in a 1 gallon container.

*Growth habit and general appearance*.—Clump-forming herbaceous perennial, mounded foliage, compact.

*Growth rate*.—Moderately vigorous.

*Outdoor plant performance*.—Use as bedding plants or in mixed-container plantings; at least tolerant to temperatures up to 35° C. and hardy to USDA zone 4.

*Size*.—Height from soil level to top of plant plane: Approximately 57.0 cm. Height from soil level to top of foliage: Approximately 12.5 cm. Width: Approximately 57.8 cm.

*Branching habit*.—No branching, basal rosettes of leaves on petioles. Number of rosettes per plant: Approximately 9.

Foliage description:

*General description*.—Moderately durable to environmental stresses. Quantity of leaves per rosette: Approximately 18. Fragrance: None. Form: Simple. Arrangement: Alternate.

*Leaves*.—Aspect: Blade is nearly perpendicular to petiole. Shape: Orbicular. Margin: Crenate, with approximately 11 shallow lobes. Apex: Rounded. Base: Cordate, sometimes moderately overlapping. Venation pattern: Palmate. Length of mature leaf: Approximately 6.1 cm. Width of mature leaf: Approximately 6.3 cm. Texture of upper surface: Slightly glossy, sparsely pubescent with short hairs of NN155D, margins moderately pubescent with short hairs of 156D. Texture of lower surface: Dull, sparsely pubescent with short hairs of NN155C to NN155D. Color of upper surface of young foliage: N200B with venation areas of 147A and N189A, and midveins of N186C. Color of lower surface of young foliage: N186D with venation of N186C. Color of upper surface of mature foliage: 198A with N200C resulting in a silver appearance, venation areas of 147A and N189A, and midveins of N186C. Color of lower surface of mature foliage: Closest to but slightly lighter than N186C with venation of N186C.

*Petiole*.—Length: Approximately 8.8 cm. Diameter: Approximately 2.0 mm. Texture: Glabrous. Color: Closest to N186C with 200B.

*Stipules*.—Two leafy stipules located at the base of each petiole. Apex: Narrow acute. Length: Approximately 1.2 cm. Width: Approximately 3.0 mm. Color: N187D.

Flowering description:

*Flowering habit*.—'Silver Blush' flowers once a year during late spring to midsummer under outdoor conditions.

*Lastingness of individual flower on the plant*.—Approximately 7 days.

Inflorescence description:

*General description*.—Type: Panicle emerging from the base of the rosette. Fragrance: None. Length or height: Approximately 52.3 cm. Width: Approximately 9.5 cm. Quantity of inflorescences per plant: Approximately 3. Quantity of flowers per inflorescence: Approximately 150.

*Peduncle*.—Strength: Moderate. Aspect: Erect to approximately 65° angle from vertical. Length: Approximately 30.0 cm. Diameter at midpoint: Approximately 2.0 to 3.0 mm. Texture: Densely pubescent. Color: 152A with an overlay of 187B.

Flower description:

*General description*.—Type: Single, campanulate, self-cleaning. Aspect: Outward to slightly drooping.

*Bud*.—Rate of opening: Generally takes 4 days for bud to progress from first color to fully open flower.

*Bud just before opening*.—Shape: Obovate. Length: Approximately 4.0 mm. Diameter: Approximately 2.0 mm. Texture: Densely glandular pubescent. Color: 53D.

*Corolla*.—Shape: Campanulate. Diameter: Approximately 4.5 mm. Depth: Approximately 6.0 mm.

*Petals*.—Quantity: 5. Arrangement: Single whorl. Shape: Linear. Appearance: Dull. Margin: Entire. Apex: Narrow acute. Base: Lower half fused into hypanthium. Length: Approximately 2.0 mm. Width: Approximately 1.0 mm. Texture of upper and lower surfaces: Glabrous. Color of upper and lower surfaces when first and fully open: 69B.

*Calyx*.—Shape: Campanulate. Diameter: Approximately 4.0 mm. Depth: Approximately 6.0 mm.

*Sepals*.—Quantity per flower: 5. Shape: Elliptic. Appearance: Dull: Margin of free portion: Entire. Apex: Broadly acute. Base: Lower half fused into hypanthium. Length: Approximately 5.0 mm. Width at rim of hypanthium: Approximately 1.5 mm. Texture of upper surface: Glabrous. Texture of lower surface: Densely glandular pubescent. Color of upper and lower surfaces: 65C with tip of 70C to 70D, hypanthium fades to 60C.

*Pedicel*.—Strength: Moderate. Length: Approximately 1.5 mm. Diameter: Less than 1.0 mm. Texture: Densely glandular pubescent. Color: N186D.

*Reproductive organs*.—Androecium: Quantity: 5 per flower. Anther shape: Ovate. Anther length: Less than 1.0 mm. Anther color: N199A. Filament length: Approximately 1.0 mm. Filament color: 155A. Pollen amount: None observed. Gynoecium: Pistil quantity: 2 per flower. Pistil length: Approximately 3.0 mm. Stigma shape: Pointed. Stigma color: NN155B. Style length: Approximately 2.75 mm. Style color: NN155B. Ovary color: 145D.

Seed and fruit production: Neither seed nor fruit production has been observed.

Disease and pest resistance: Resistance to pathogens and pests common to *Heuchera* has not been observed.

What is claimed is:

1. A new and distinct cultivar of *Heuchera* plant named 'Silver Blush', substantially as herein shown and described.

* * * * *